US007614293B2

(12) United States Patent
Kuno et al.

(10) Patent No.: US 7,614,293 B2
(45) Date of Patent: Nov. 10, 2009

(54) METHOD OF EVALUATING ADHESION PROPERTY, LOW-ADHESION MATERIAL, AND MOLD FOR MOLDING RESIN

(75) Inventors: Takaki Kuno, Kyoto (JP); Keiji Maeda, Kyoto (JP); Yoshinori Noguchi, Kyoto (JP); Satoshi Kitaoka, Nagoya (JP); Naoki Kawashima, Nagoya (JP); Seiichi Suda, Nagoya (JP); Masato Yoshiya, Nagoya (JP); Norio Yamaguchi, Nagoya (JP)

(73) Assignees: Towa Corporation, Kyoto-Shi, Kyoto (JP); Japan Fine Ceramics Center, Nagoya-Shi, Aichi (JP)

( * ) Notice: Subject to any disclaimer, the term of this patent is extended or adjusted under 35 U.S.C. 154(b) by 549 days.

(21) Appl. No.: 10/571,683

(22) PCT Filed: Mar. 3, 2005

(86) PCT No.: PCT/JP2005/003577

§ 371 (c)(1),
(2), (4) Date: Mar. 13, 2006

(87) PCT Pub. No.: WO2005/092587

PCT Pub. Date: Oct. 6, 2005

(65) Prior Publication Data
US 2008/0254286 A1    Oct. 16, 2008

(51) Int. Cl.
*G01N 19/04* (2006.01)
(52) U.S. Cl. .................................... 73/150 A
(58) Field of Classification Search ............... 73/150 A, 73/150 R, 842; 425/352
See application file for complete search history.

(56) References Cited

FOREIGN PATENT DOCUMENTS

| JP | 60-103078 A | 6/1985 |
|---|---|---|
| JP | 3-38314 A | 2/1991 |
| JP | 5-215668 A | 8/1993 |
| JP | 7-329099 A | 12/1995 |
| JP | 11-64211 A | 3/1999 |
| JP | 2004-25677 A | 1/2004 |

(Continued)

OTHER PUBLICATIONS

Bardina, N.G. "Anodic oxide films." Russian Chemical Reviews. Vo. 35. No. 5. pp. 286-295. May 1964.*

(Continued)

*Primary Examiner*—Lisa M Caputo
*Assistant Examiner*—Punam Patel
(74) *Attorney, Agent, or Firm*—Birch, Stewart, Kolasch & Birch, LLP

(57) ABSTRACT

A mold surface of an upper mold with which a fluid resin comes into contact has an oxide therein. The oxide contains a metal cation and an ion. Field strength is calculated based on a valence of the metal cation and ionic radius of the ion. Based on predetermined relationship established between a value of the field strength and adhesion strength between a cured resin and the mold surface, releasability between the cured resin and the mold surface is evaluated. Thereby, a method of evaluating releasability between the cured resin and the mold surface is established. With this evaluation method, a material with high releasability can readily be provided. Further, if the material with high releasability is used for the mold surface of the upper mold, a mold for molding a resin having excellent releasability can be obtained.

1 Claim, 3 Drawing Sheets

FOREIGN PATENT DOCUMENTS

| | | |
|---|---|---|
| KR | 2002-0008759 A | 1/2002 |
| SU | 1073691 A * | 2/1984 |

OTHER PUBLICATIONS

Erdimer, A. "Solid lubricants and self-lubricating films." Modern Tribilogy Handbook. Ed. Bhushan. Bharat. Washington, DC: CRC, 2001. vol. 2, Section III, Ch. 22.4.3.*

A. Erdemir. "A crystal-chemical approach to lubrication by solid oxides." Tribology Letters 8 (2000) 97-102.*

Yu Qiang et al., "Research on Preparation of Palladium Inorganic Composite Membrane by New Rare Earths—Electroless Plating Technique", Journal of Nanchang University (Engineering & Technology), vol. 24, No. 1, pp. 51-54, Mar. 2002.

* cited by examiner

METHOD OF EVALUATING ADHESION PROPERTY, LOW-ADHESION MATERIAL, AND MOLD FOR MOLDING RESIN

TECHNICAL FIELD

The present invention relates to a method of evaluating an adhesion property between an organic substance and a surface of a member, a low-adhesion material having a low adhesion property with respect to an organic substance, and a mold for molding a resin having a mold surface made of the low-adhesion material.

BACKGROUND ART

Conventionally, transfer molding or injection molding has been used for molding a resin. These techniques use a mold for molding a resin. The mold is provided with a resin flow channel and a cavity. A fluid resin is injected into the cavity through the resin flow channel. When the fluid resin in the cavity is cured, a cured resin is formed. As a result, a molded body having the cured resin is completed.

A thermosetting resin is used as the fluid resin described above, and tool steel is used as a material for the mold. In this case, an adhesion property between the cured resin and the surface of the mold (mold surface) should be reduced for easy removal of the molded body. In other words, releasability between the cured resin and the mold surface should be improved.

As a surface reforming material facilitating release of a mold from a cured resin, an organic material such as polytetrafluoroethylene or silicone rubber having a good non-wetting (dewetting) characteristic, that is, a low wetting characteristic, with respect to a fluid resin is considered to be promising. A method of molding a resin using these organic materials is disclosed in Japanese Patent Laying-Open No. 07-329099 (on page 3 to page 4). In this method, firstly, the organic material described above is sprayed or applied onto a mold surface. Thereafter, the organic material is dried, and thus coating of the organic material on the mold surface is completed.

Further, there may be a case where a chip-type electronic component such as an LSI chip mounted on a lead frame, a printed board, or the like (hereinafter will be referred to as a "chip") is sealed with a resin. In this case, a thermosetting resin containing a ceramic filler, for example, an epoxy resin is used as a fluid resin. Since the filler wears the mold surface, a method of forming on the mold surface an inorganic material with high hardness having wear resistance is employed. In the method, the mold surface is coated with an inorganic material with high hardness excellent in wear resistance such as Cr, TiC, or CrN, by means of plating, PVD (Physical Vapor Deposition), CVD (Chemical Vapor Deposition), or the like.

Also, Japanese Patent Laying-Open No. 2004-25677 proposes a method of emitting a gas component contained in a fluid resin out of a mold for molding a resin made of a porous material having a three-dimensional communicating hole, through the communicating hole (on page 5 to page 6, and in FIGS. 1 and 2).

However, the conventional technique described in the foregoing Japanese Patent Laying-Open No. 2004-25677 (on page 5 to page 6, and in FIGS. 1 and 2) has problems as described below.

Firstly, when the mold is made of a conventional material, a cured resin is likely to stick to a mold surface. For this reason, the mold surface should be cleaned periodically to allow the cured resin to be always easily removed from the mold. Therefore, frequent maintenance is required.

Secondly, numerous eject mechanisms are required to remove a molded body from the mold. Thus, the mold becomes larger and has a complicated structure.

Thirdly, when the mold surface is coated with an organic material such as polytetrafluoroethylene or silicone rubber, these organic materials are likely to be worn by a filler contained in the fluid resin. Therefore, it is difficult to use these organic materials singly as a material for reforming the mold surface.

Fourthly, when the mold surface is coated with an inorganic material with high hardness excellent in wear resistance such as Cr, TiC, or CrN, releasability between the cured resin and the mold surface is insufficient because these inorganic materials do not have a sufficient non-wetting characteristic with respect to a fluid resin. Further, when the mold for molding a resin is made of a porous material, the range of selection for a material excellent in releasability is narrow.

Furthermore, there is a problem resulting from the fact that a method of evaluating releasability, in other words, a method of evaluating an adhesion property of a mold surface with respect to a cured resin has not been established. To explain this problem, two processes assumed as processes through which a cured resin sticks to a mold surface will now be described.

A first process is a process in which a silane coupling agent contained in a fluid resin made of a thermosetting resin plays a role in the sticking of a cured resin to a mold surface. The silane coupling agent is added to the thermosetting resin. The silane coupling agent contains an alkoxy group (alkoxyl group). The alkoxy group reacts with a hydroxyl group existing in the surface of a filler. Thereby, an alcohol is produced, and the alkoxy group is chemically absorbed into the surface of the filler. Therefore, an absorption layer is formed in the surface of the filler. As a result, a wetting characteristic between the filler and the fluid resin is enhanced due to the absorption layer.

The chemical absorption described above occurs not only in the surface of the filler but also in the surface of an oxide layer of the mold surface. In this case, firstly, moisture in the air is absorbed into the surface of the oxide layer existing in the mold surface, and thus a hydroxyl group is formed in the surface of the oxide layer. Next, the hydroxyl group reacts with an alkoxy group, and thus an absorption layer is formed in the surface of the oxide layer. As a result, a wetting characteristic between the mold surface and the fluid resin is enhanced. Next, the thermosetting resin constituting the fluid resin is heated to form a cured resin. In this occasion, the sticking strength between the mold surface and the cured resin is increased due to the enhanced wetting characteristic between the mold surface and the fluid resin.

A second process is a process in which an amine-based curing agent contained in a fluid resin made of a thermosetting resin plays a role in the sticking of a cured resin to a mold surface. In this process, the amine-based curing agent reacts with a hydroxyl group in the surface of an oxide layer to form an amine complex. Thereafter, curing of the thermosetting resin on the surface of the oxide progresses due to the presence of the amine complex. As a result, the oxide layer and the thermosetting resin firmly stick together via the amine complex.

In the two processes described above, a change occurs in releasability between the cured resin and the mold surface, more generally speaking, an adhesion property between the cured resin and the surface of a member. As a physical factor of the change in the adhesion property, there is known a possibility that surface roughness is involved in the change.

Further, as a chemical factor of the above change, there is known a possibility that hydrogen bond is involved in the change. However, a method of strictly evaluating an adhesion property between a cured resin and the surface of a member has not been established yet. Therefore, in a conventional method of evaluating an adhesion property, samples of a plurality of oxides should be prepared and tested individually, and thus there is a problem that the method requires much time and effort.

Patent Document 1: Japanese Patent Laying-Open No. 07-329099 (page 3 to page 4)

Patent Document 2: Japanese Patent Laying-Open No. 2004-25677 (page 5 to page 6, FIGS. 1 and 2)

DISCLOSURE OF THE INVENTION

Problems to be Solved by the Invention

The present invention has been made in view of the aforementioned problems, and one object of the present invention is to provide a method of evaluating an adhesion property between an organic substance and a surface of a member. Another object of the present invention is to provide a low-adhesion material having a low adhesion property with respect to an organic substance. Still another object of the present invention is to provide a mold for molding a resin having excellent releasability.

Means for Solving the Problems

A method of evaluating an adhesion property of the present invention is a method of evaluating an adhesion property between an organic substance and a surface of a member having an oxide therein. In the method of evaluating an adhesion property of the present invention, a value of field strength is determined based on a valence of a metal cation (a positive metal ion) contained in the oxide and an ionic radius of an ion (including the metal cation) contained in the oxide, and the adhesion property is evaluated based on the value of the field strength. According to this method, the adhesion property between the organic substance and the surface of the member can be evaluated appropriately.

Further, a low-adhesion material of the present invention is a material having a value of field strength determined by the method of evaluating an adhesion property described above within a predetermined range. Thus, a low-adhesion material having a desired value of adhesion strength with respect to a predetermined substance can be obtained.

In the low-adhesion material described above, it is desirable that the valence of the metal cation is not less than 3. Thereby, a substance hard to absorb water, carbon dioxide, or the like in the air, that is, a chemically stable substance, is used as the oxide described above, and thus an excellent adhesion property can be maintained for a long period of time.

In the low-adhesion material described above, it is desirable that the ion includes an oxygen ion, and the predetermined range is not less than 0.50 and not more than 0.65. This can suppress firm sticking of the oxide and a thermosetting resin.

Further, in the low-adhesion material described above, it is desirable that the oxide is a porous material. Thereby, weight reduction in the low-adhesion material can be achieved.

In the low-adhesion material described above, it is desirable that the oxide includes $Y_2O_3$. Thereby, the low-adhesion material can readily be available, and cost reduction in the low-adhesion material can be achieved.

A mold for molding a resin of the present invention has a mold surface made of the low-adhesion material described above. The mold surface of the mold for molding a resin has excellent releasability with respect to a resin.

In the mold for molding a resin described above, it is desirable that the valence of the metal cation is not less than 3. Thereby, the excellent adhesion property described above can be maintained for a long period of time.

Further, in the mold for molding a resin described above, it is desirable that the ion includes an oxygen ion, and the predetermined range is not less than 0.50 and not more than 0.65. Thereby, firm sticking of the oxide and the resin can be suppressed, and thus releasability between the mold surface and the cured resin can further be improved.

Further, in the mold for molding a resin described above, it is desirable that the oxide is a porous material. Thereby, a gas component contained in the fluid resin is emitted from numerous holes, and thus formation of a void in a molded body can be suppressed. Furthermore, the molded body can be ejected from the mold for molding a resin by the emission of high-pressure gas such as compression air from openings in the mold surface. In addition, weight reduction in the mold for molding a resin can be achieved.

In the mold for molding a resin described above, it is desirable that the oxide includes $Y_2O_3$. Thereby, cost reduction in the mold for molding a resin can be achieved.

The foregoing and other objects, features, aspects and advantages of the present invention will become apparent from the following detailed description of the present invention when taken in conjunction with the accompanying drawings.

DESCRIPTION OF THE REFERENCE SIGNS

1, 10 upper mold (mold for molding a resin), 2 lower mold, 3 material with high releasability (low-adhesion material), 4 resin flow channel, 5 cavity, 6 mold surface (surface), 7 substrate, 8 chip, 9 wire, 11 mold main body, 12 mold-releasing layer, 13, 17 low-adhesion material, 14 base material, 15 communicating hole, 16 opening, 18 conductive layer.

BEST MODES FOR CARRYING OUT THE INVENTION

First Embodiment

Figure 1:
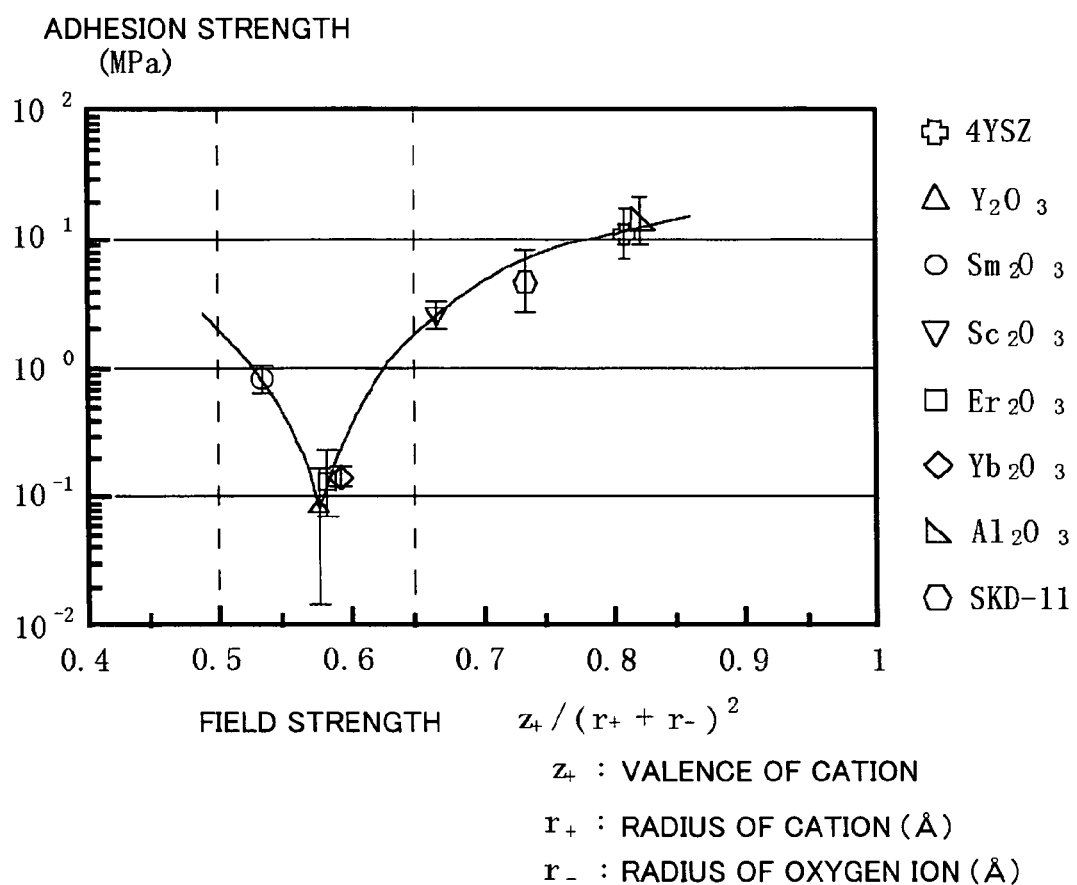
FIG. 1 illustrates a method of evaluating an adhesion property of a mold for molding a resin in a first embodiment, showing relationship between field strength and adhesion strength (adhesion property).

Firstly, referring to FIG. 1, explanation will be given on a method of evaluating an adhesion property between an organic substance and a surface of a member as well as a low-adhesion material in a first embodiment. FIG. 1 shows an adhesion property of a cured resin made of an organic substance. In FIG. 1, a horizontal axis represents magnitude of field strength. It is to be noted that an oxide is contained in the surface of a portion of the member to be evaluated with which a fluid resin comes into contact. The oxide contains a metal cation and an ion.

The field strength shown in FIG. 1 is a value calculated based on a valence of the metal cation and a radius of the ion. In FIG. 1, a vertical axis (logarithmic scale) represents magnitude of adhesion strength. The adhesion strength is a measured value of adhesion strength between the cured resin and the surface of the member.

The value of the field strength is calculated based on an expression $z_+/(r_+ + r_-)^2$ as shown in FIG. 1. In this expression, $z_+$ represents the valence of the metal cation, $r_+$ represents an ionic radius (unit: Å) of the metal cation, and $r_-$ represents an ionic radius (unit: Å) of an anion (specifically, an oxygen ion). It is to be noted that, other than the expression described above, the expression for calculating the field strength may be an expression based on a valence z of the metal cation and an ionic radius r, such as $z/r$.

The adhesion strength is measured by an experiment which will be described below.

Firstly, a cylinder-shaped oxide having an outer diameter of φ13.585 mm is prepared. Next, an end surface of the oxide is mirror polished. Thereafter, the oxide is fit into a pot (φ13.6 mm) of a mold for molding a resin. Next, an epoxy-based solid resin material is fit into the pot, and then the mold for molding a resin is closed. Next, the solid resin material is heated at a predetermined temperature under a predetermined pressure (10 MPa). As a result, the solid resin material is melted. Thereafter, the melted solid resin material is cured. The cured resin is thus obtained through the process as described above.

Next, a tensile test is performed on a molded body in which the cured resin and the oxide stick together. Further, a tensile load when an interface between the cured resin and the oxide has been separated is divided by a cross sectional area of the interface to calculate adhesion strength between the cured resin and the oxide.

FIG. 1 plots relationship between the field strength calculated using the above expression and the adhesion strength obtained through the above experiment for each of four kinds of oxides, that is, 4YSZ (Yttria-Stabilized Zirconia), $Al_2O_3$, $Y_2O_3$, and $Sc_2O_3$.

For comparison, FIG. 1 also plots relationship between field strength and adhesion strength of mirror polished tool steel (SKD-11).

A valence of a metal cation and a value of an ionic radius for $ZrO_2$ as a simple substance are used as a valence of a metal cation and a value of an ionic radius for 4YSZ, respectively. Further, a valence of a metal cation and a value of an ionic radius for $Fe_2O_3$ are used as a valence of a metal cation and a value of an ionic radius for SKID-11, respectively.

From the result of the above experiment, it is found that there is a minimum value in the relationship between the field strength and the adhesion strength, as shown in FIG. 1. It is to be noted that the adhesion strength shown in FIG. 1 represents adhesion strength (adhesion property) between the cured resin (thermosetting resin) and the surface of a member in a case where the oxide described above exists in the surface of the member.

Further, it is found from FIG. 1 that, when an oxide existing in the surface of a member has a value of the field strength within a predetermined range, the adhesion strength between the cured resin and the surface of the member is low. The reason is attributable to the fact that will be described below.

When the value of the field strength is within a predetermined range, moisture absorption to the surface of the oxide, that is, to the surface of the member, is suppressed, and thus formation of a hydroxyl group in the surface of the member is suppressed. Thereby, reaction of the hydroxyl group and an alkoxy group is suppressed, reducing a wetting characteristic between the surface of the member and the fluid resin. Further, reaction of an amine-based curing agent and the hydroxyl group is suppressed, and thus curing of the thermosetting resin on the surface of the member is suppressed. As a result, the oxide and the thermosetting resin are suppressed from firmly sticking together.

Therefore, it is considered that, when it is necessary to suppress the thermosetting resin from sticking to the surface of the oxide, that is, the surface of the member, it is satisfactory to suppress the formation of the hydroxyl group in the surface of the oxide. For that purpose, it is necessary to decrease the strength of Lewis acid site of the metal cation constituting the oxide to suppress the absorption of moisture (the formation of the hydroxyl group) with respect to the surface of the oxide. Further, it is necessary to reduce the density of the hydroxyl group formed in the surface of the oxide.

Furthermore, consideration of whether or not the cured resin is likely to stick to the surface of the oxide, that is, the surface of the member, leads to evaluation of an adhesion property between the cured resin and the oxide. Therefore, it is considered that the adhesion property between the cured resin and the oxide formed in the surface of the member can be evaluated based on the relationship shown in FIG. 1, by means of a method which will be described below. Note that, in the description below, the adhesion property, that is, releasability between the cured resin and the mold surface of the mold for molding a resin is evaluated.

Firstly, a value of adhesion strength (adhesion property) for achieving required releasability, that is, an upper limit value of the adhesion strength, is predetermined. Next, based on a curve representing the relationship obtained from the result of the experiment shown in FIG. 1, a range of field strength corresponding to the upper limit value of the adhesion strength is determined as a range of a reference value for comparison. Next, the field strength of the oxide to be evaluated is calculated, and the calculated value is compared with the range of the reference value for comparison. As a result, if the calculated value of the field strength is within the range of the reference value for comparison, the oxide can be evaluated to have the required releasability.

In this evaluation, in order to obtain the required releasability, the upper limit value of the adhesion strength is set at 2 MPa. Further, it can be seen from FIG. 1 that the value of the field strength corresponding to the adhesion strength of not more than 2 MPa is approximately in a range of not less than 0.50 and not more than 0.65. Thus, the reference value for comparison of the field strength is determined to be not less than 0.50 and not more than 0.65. Therefore, as for an oxide other than the oxides shown in FIG. 1, if a calculated value of its field strength is in a range of not less than 0.50 and not more than 0.65, the oxide is evaluated to have the required releasability. In this manner, whether or not an oxide has high releasability, that is, whether or not the oxide is a low-adhesion material, can be determined only by calculation without performing an experiment, based on valence $z_+$ and ionic radius $r_+$ of a metal cation and ionic radius $r_-$ of an oxygen ion. Further, whether or not an oxide has high releasability can also be determined only by calculation based on valence z and ionic radius r of a metal cation.

As a result of the above evaluation method, it is preferable to use an oxide having field strength within the range of the reference value for comparison described above and having a valence of a metal cation contained therein of not less than 3, because, if the valence of the metal cation is not less than 3, the oxide is a substance hard to absorb water or carbon dioxide in the air, that is, a chemically stable substance. Therefore, it becomes easier to select an oxide having durability as a low-adhesion material forming at least the mold surface or the entire mold for molding a resin.

Further, from the result of calculating the values of the field strength in a plurality of oxides, it has been found that there exist oxides having the field strength within the range of not less than 0.50 and not more than 0.65, such as $Y_2O_3$ (0.58), $Gd_2O_3$ (0.56), $Sm_2O_3$ (0.55), $Eu_2O_3$ (0.55), $Er_2O_3$ (0.58), $Yb_2O_3$ (0.59), and $Lu_2O_3$ (0.60). Note that the number within the parenthesis represents a calculated value of the field strength.

Of the oxides described above, it is preferable to use $Y_2O_3$, $Er_2O_3$, or $Yb_2O_3$ as a material forming the mold surface. Further, taking availability, cost, and the like into consideration in addition to a low adhesion property, $Y_2O_3$ is most preferable as a low-adhesion material.

On the other hand, if the value of the field strength of an oxide is not in the range of the reference value for comparison of not less than 0.50 and not more than 0.65, the oxide is considered as not appropriate as a low-adhesion material forming the mold surface, due to the reasons which will be described below.

Firstly, when the field strength of an oxide is less than 0.50, the oxide existing in the mold surface is likely to absorb water or carbon dioxide in the air. A hydrate or a carbonate produced by a reaction of the oxide and water or carbon dioxide is stable. Therefore, due to the above reaction, it becomes difficult for the oxide to maintain its structure. Further, since a reaction due to a silane coupling agent or an amine-based curing agent occurs in the surface of the hydrate, the sticking of the thermosetting resin to the mold surface is significantly enhanced.

Secondly, when the field strength of an oxide is more than 0.65, bond between a cation contained in the oxide existing in the mold surface and a hydroxyl group becomes firmer, and the bond site has a higher density. Therefore, the sticking of the thermosetting resin to the mold surface due to a silane coupling agent or an amine-based curing agent is further enhanced.

Next, explanation will be given on a method of manufacturing a low-adhesion material in the present embodiment.

Firstly, powder of a predetermined oxide, for example powder of $Y_2O_3$ is prepared as a material. Next, the powder of $Y_2O_3$ is molded under a predetermined pressure, using a mold. If a mold in an appropriate shape is used in this step, a low-adhesion material having a concave portion corresponding to a resin flow channel and a cavity (see a resin flow channel 4 and a cavity 5 in FIG. 2) is manufactured. Next, the molded $Y_2O_3$ (a mixture) is molded by pressure, using CIP (Cold Isostatic Pressing). Then, the $Y_2O_3$ molded by pressure is sintered at a predetermined temperature for a predetermined period of time. Thereby, a sintered compact of the oxide $Y_2O_3$ is obtained. Further, a burned material may be sintered by pressure, using HP (Hot Press) or HIP (Hot Isostatic Pressing), in order to enhance relative density of the burned material.

Although the range of the reference for comparison of the field strength is determined to be not less than 0.50 and not more than 0.65 in the above description, this range of the reference value for comparison may be changed depending on such as the application of the low-adhesion material or the characteristic of the cured resin. Further, the method of evaluating an adhesion property in the present embodiment may be used to evaluate an adhesion property between an organic substance other than a cured resin and a surface of a member.

Second Embodiment

Figure 2:
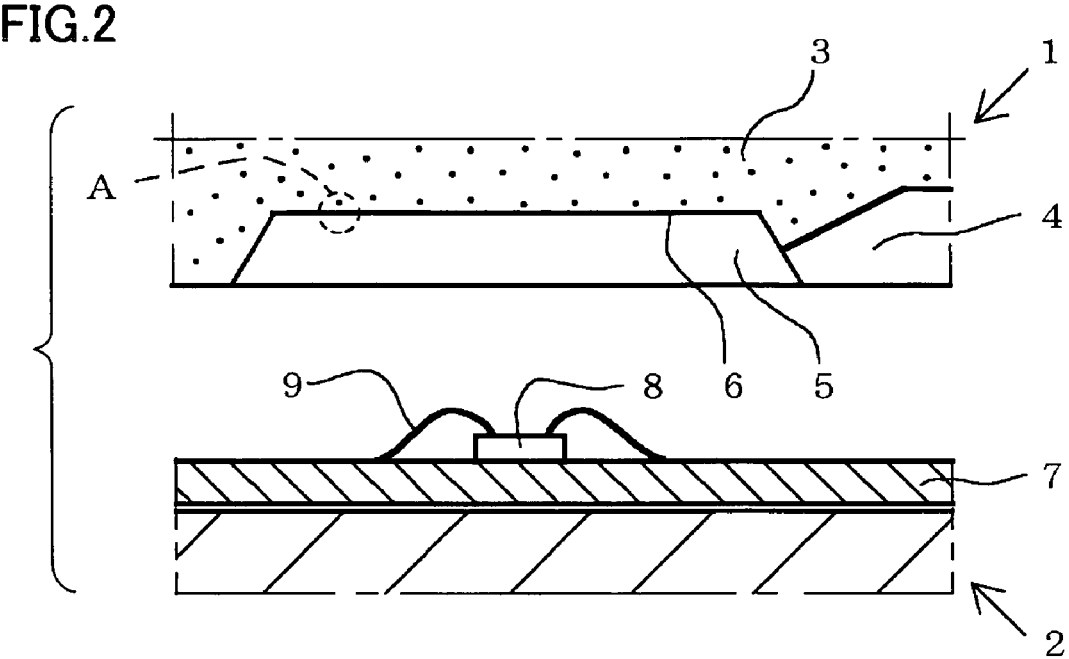
FIG. 2 is a cross sectional view showing a mold for molding a resin in a second embodiment.
Figure 3:
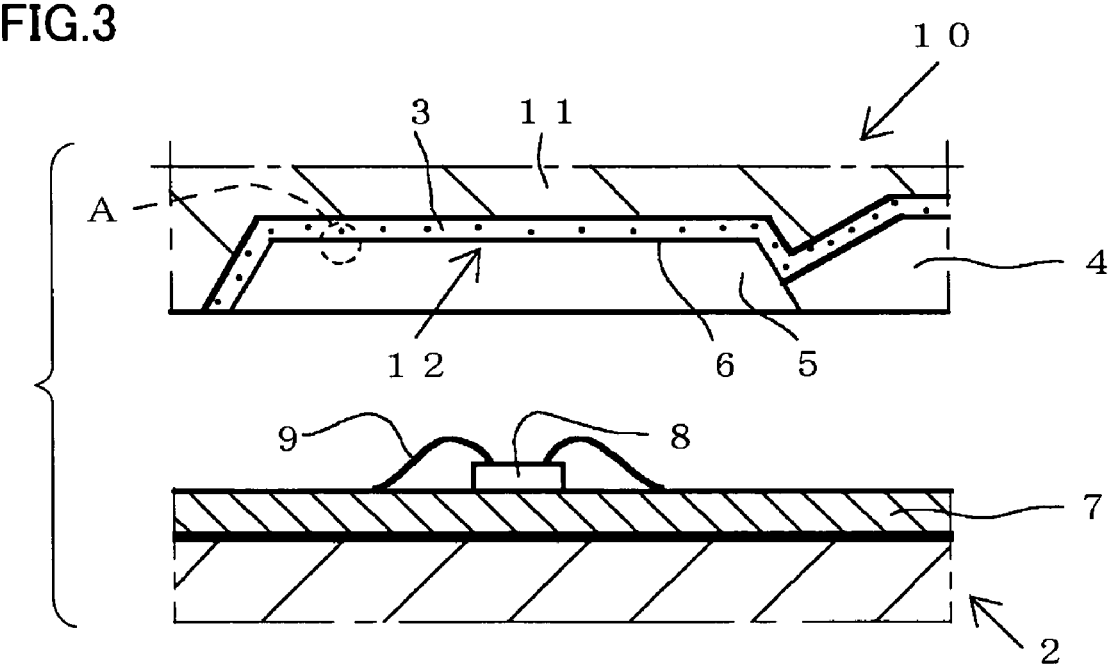
FIG. 3 is a cross sectional view showing a mold for molding a resin in a modification.

Next, referring to FIGS. 2 and 3, a mold for molding a resin in an embodiment of the present invention will be described. FIGS. 2 and 3 are cross sectional views showing a mold for molding a resin in the present embodiment and its modification, respectively, both of which are exaggerated for ease of illustration. In the present embodiment, as an example of resin molding, explanation will be given on transfer molding for sealing a chip mounted on a substrate with a resin.

In this sealing with a resin, firstly, a wired chip is accommodated in a cavity. Next, with the mold closed, the cavity is filled with a fluid resin. Thereafter, the fluid resin is cured to form a cured resin. As a result, a molded body (package) having a substrate and the cured resin is completed.

As shown in FIG. 2, the mold for molding a resin in the present embodiment includes an upper mold 1 and a lower mold 2. Upper mold 1 corresponds to the mold for molding a resin in the present invention. Upper mold 1 is formed of a material with high releasability 3 made of the low-adhesion material (oxide) of the present invention.

Upper mold 1 is provided with a resin flow channel 4 through which the fluid resin (not shown) flows, and a cavity 5 to be filled with the fluid resin. Cavity 5 and resin flow channel 4 constitute a concave portion. A surface of resin flow channel 4 and a surface of cavity 5 constitute a mold surface 6 with which the fluid resin comes into contact. Specifically, material with high releasability 3 is exposed at mold surface 6.

On the other hand, lower mold 2 is formed of such as tool steel. A substrate 7 including a lead frame, a printed board, or the like is placed on lower mold 2. A chip 8 is mounted on substrate 7. A wire 9 electrically connects an electrode (not shown) of substrate 7 and an electrode (not shown) of chip 8.

Next, explanation will be given on operation of the mold for molding a resin shown in FIG. 2.

Firstly, substrate 7 is placed on lower mold 2. Next, substrate 7 is fixed to lower mold 2 by means of absorption or the like. Thereafter, upper mold 1 is lowered, and thus closing of upper mold 1 and lower mold 2 is completed. Next, the fluid resin made of a thermosetting resin and having a predetermined viscosity is pushed by a plunger (not shown). Thereby, the fluid resin is injected into cavity 5 through resin flow channel 4.

Next, the fluid resin is heated by a heater (not shown) provided for each of upper mold 1 and lower mold 2. As a result, the fluid resin is cured. The cured resin is thus formed through the steps as described above. Next, upper mold 1 is raised, and thus opening of upper mold 1 and lower mold 2 is completed. Thereafter, a molded product is taken out of the mold for molding a resin. In the molded product, substrate 7, chip 8, and wire 9 are sealed with the cured resin in a unified manner.

In the mold for molding a resin in the present embodiment, upper mold 1 which comes into contact with the fluid resin is formed of material with high releasability 3 made of the low-adhesion material described in the first embodiment. Specifically, mold surface 6 of upper mold 1 with which the fluid resin comes into contact is formed of material with high releasability 3. Further, since material with high releasability 3 has excellent releasability with respect to the cured resin, the mold for molding a resin in the present embodiment does not require an eject mechanism. Furthermore, since material with high releasability 3 is a chemically stable substance, it can maintain excellent releasability for long period of time. As a result, frequency of cleaning can be reduced. Further, since ceramics made of an oxide such as $Y_2O_3$ has excellent wear resistance, the problem regarding the wear of an organic material caused when the mold surface is coated with the organic material is solved. Furthermore, the mold for molding a resin in the present embodiment is excellent in releasability, when compared to a mold for molding a resin in which the mold surface is coated with an inorganic material such as Cr, Tic, or CrN.

The mold for molding a resin in the present embodiment is manufactured by performing processing such as providing a mounting hole in the low-adhesion material of the first embodiment. Note that, in order to manufacture a mold in a precise shape, precision processing by cutting may be provided on the low-adhesion material of the first embodiment.

Next, referring to FIG. 3, explanation will be given on a mold for molding a resin in a modification.

The mold for molding a resin in a modification of the present embodiment includes an upper mold 10 instead of upper mold 1. Upper mold 10 includes a mold main body 11 made of a material for a conventional mold for molding a resin (such as tool steel), and a mold-releasing layer 12 made of the low-adhesion material of the present invention provided on a surface of mold main body 11. Mold-releasing layer 12 is formed by a well-known method such as PVD, CVD, sputtering, or ion plating, for example.

According to the mold for molding a resin in the modification, since mold surface 6 is formed of mold-releasing layer 12, an effect similar to that obtained by the mold for molding a resin shown in FIG. 2 can be obtained. It is to be noted that mold main body 11 may be formed of ceramics instead of a metal material.

Third Embodiment

Figure 4:
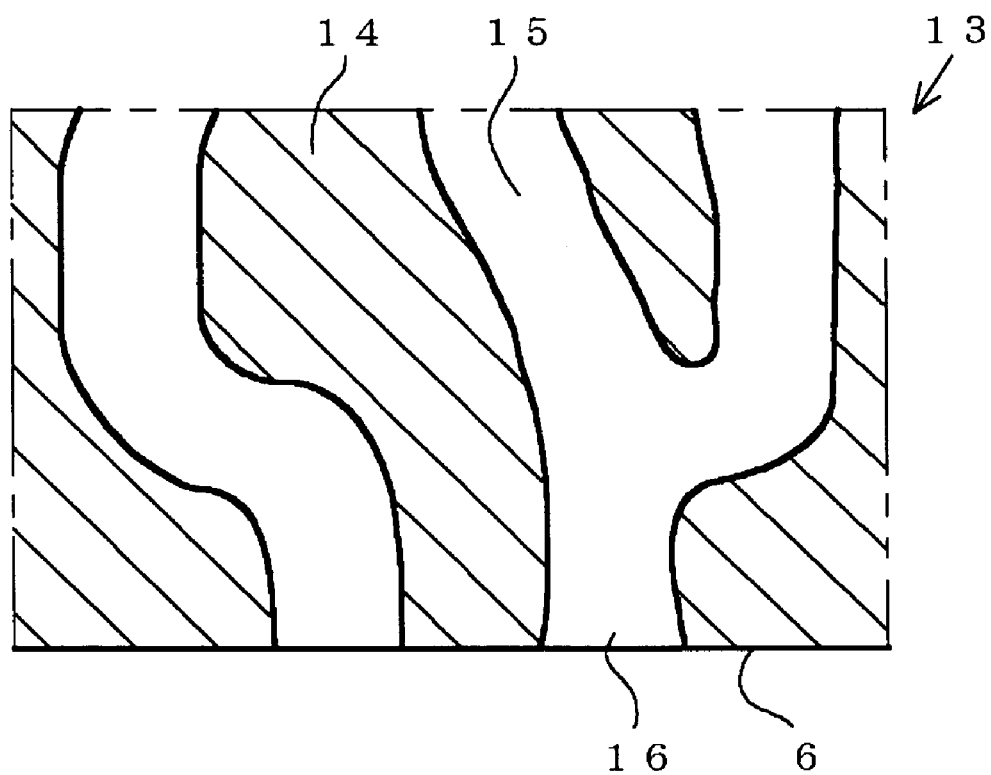
FIG. 4 is an enlarged cross sectional view showing the proximity of a mold surface of a mold for molding a resin in a third embodiment.
Figure 5:
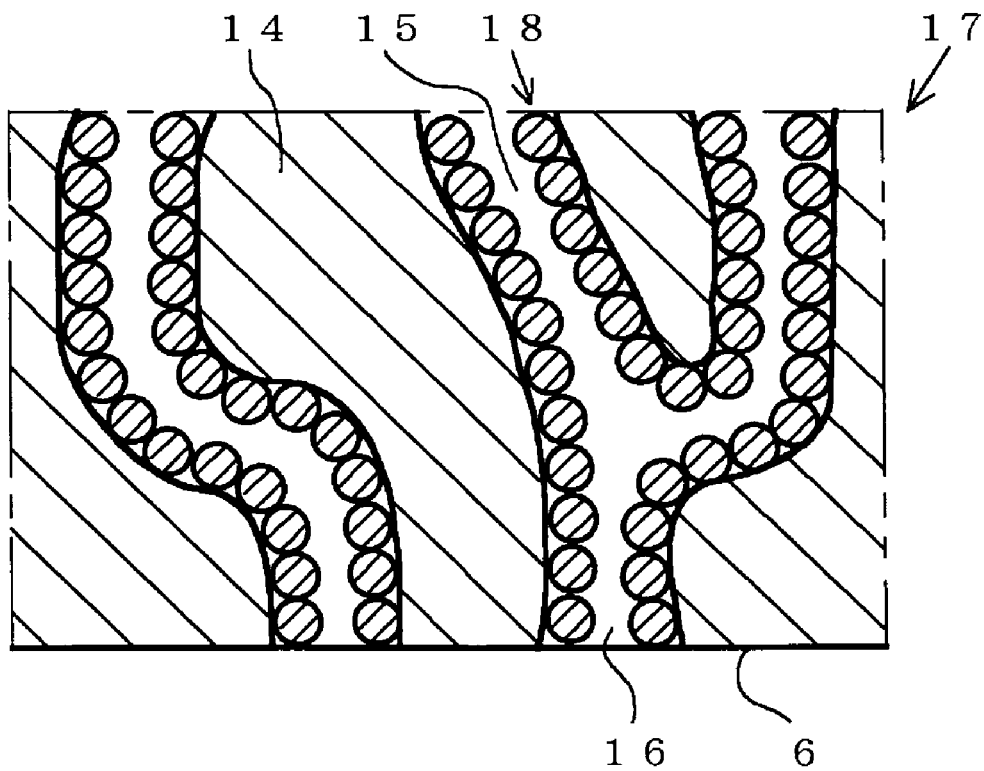
FIG. 5 is an enlarged cross sectional view showing the proximity of a mold surface of a mold for molding a resin in a modification.

Next, referring to FIGS. 4 and 5, explanation will be given on a mold for molding a resin using a low-adhesion material of a third embodiment and its modification. FIGS. 4 and 5 are enlarged cross sectional views showing the proximity of a mold surface of a mold for molding a resin in the present embodiment and the proximity of a mold surface of a mold for molding a resin in the modification, respectively. FIGS. 4 and 5 correspond to enlarged cross sectional views of parts designated by a reference letter A in FIGS. 2 and 3, respectively.

In the mold for molding a resin in the present embodiment, material with high releasability 3 of upper mold 1 shown in FIG. 2 and of upper mold 10 shown in FIG. 3 is a porous material (a low-adhesion material 13 in FIG. 4). Further, as shown in FIG. 4, low-adhesion material 13 in the present embodiment has a base material 14 made of the low-adhesion material (oxide) described in the first embodiment, and a three-dimensional communicating hole 15 having an average diameter of 10 nm to 1000 nm. Since communicating hole 15 reaches mold surface 6, a plurality of openings 16 each having an average diameter of 10 nm to 1000 nm are formed in mold surface 6. The average diameter of the plurality of openings 16 is determined to allow passage of a gas component (including water vapor) contained in the cavity and the fluid resin but not to allow passage of a component other than gas, such as a particle of the fluid resin.

In the present embodiment, low-adhesion material 13 shown in FIG. 4 is used as material with high releasability 3 shown in FIGS. 2 and 3. Further, mold main body 11 shown in FIG. 3 is made of a material having three-dimensional porousness, specifically, a metal material, ceramics, or the like having numerous three-dimensional communicating holes.

According to the mold for molding a resin in the present embodiment, an effect resulting from the excellent releasability between the molded body and mold surface 6 can be obtained, as in the mold for molding a resin in the second embodiment. In addition, effects as will be described below can also be obtained.

Firstly, since the gas component contained in the fluid resin is emitted out of the mold for molding a resin through communicating hole 15, occurrence of a void in the molded body is suppressed. This effect can further be enhanced by reducing pressure in resin flow channel 4 and cavity 5 while closing upper mold 1 shown in FIG. 2 or upper mold 10 shown in FIG. 3 and lower mold 2, or after upper mold 1 or 10 and lower mold 2 are closed. Secondly, since compressed air and the like can be emitted from openings 16 in mold surface 6 into each of resin flow channel 4 and cavity 5 shown in FIG. 2, the molded body can surely be ejected from mold surface 6. Thirdly, weight reduction in the low-adhesion material and the mold for molding a resin in can be achieved.

Next, explanation will be given on a mold for molding a resin in a modification of the present embodiment having a low-adhesion material shown in FIG. 5. In a low-adhesion material 17 in the modification shown in FIG. 5, a conductive layer 18 which can generate heat when current flows therethrough is formed on an inner wall of communicating hole 15. Since the mold for molding a resin is formed of such low-adhesion material 17, the mold for molding a resin itself can generate heat. Specifically, by supplying current directly to low-adhesion material 17 using a power source, Joule heat can be generated in conductive layer 18 formed on the inner wall of communicating hole 15. It is also possible to utilize the conductivity of low-adhesion material 17 to allow conductive layer 18 to generate heat by means of IH (Induction Heating).

It is to be noted that, in the mold for molding a resin in the modification, low-adhesion material 17 shown in FIG. 5 is used as material with high releasability 3 in FIGS. 2 and 3. Further, in the mold for molding a resin shown in FIG. 3, mold main body 11 is made of a material having three-dimensional porousness, specifically, a metal material, ceramics, or the like having numerous three-dimensional communicating holes.

Next, explanation will be given on a method of manufacturing low-adhesion material 17 having porousness and conductivity.

Firstly, oxide particles and carbon particles are mixed at a predetermined ratio by ball milling. Next, a mixture made of the mixed materials is subjected to vibrated-fluidized drying. Thereafter, the dried mixture is processed to have a uniform particle size using a screen with an appropriate mesh. Next, the mixture having uniform-sized particles is molded using a mold. Thereafter, the molded mixture is molded by pressure by means of CIP. Then, the mixture molded by pressure is sintered at a predetermined temperature for a predetermined period of time.

In the mold for molding a resin in the present modification, the mixture is burned in a condition in which an atmosphere within a burning furnace has a reduced pressure, that is, in a so-called vacuum condition. Next, sintered low-adhesion material 17 is taken out from the burning furnace. Thereby, low-adhesion material 17 having a desired shape as well as porousness and conductivity is completed. If a more precise shape is required, precision processing by means of such as electrical discharge machining may be performed on low-adhesion material 17, utilizing conductive layer 18 of low-adhesion material 17. Further, cutting may be performed on low-adhesion material 17. Through the process as described above, for example upper mold 1 shown in FIG. 2 is completed.

According to the method of manufacturing low-adhesion material 17 described above, in the step of burning the mixture in a vacuum condition, CO gas generated by carbon reduction reaction is emitted from the mixture during the burning. Thereby, a path of the CO gas emission remains as communicating hole 15 having a uniform and minute diameter in the sintered compact after the burning, that is, low-adhesion material 17. Communicating holes 15 having a uniform diameter of not more than 1000 nm are formed with being dispersed uniformly in low-adhesion material 17. Further, on the inner wall of each communicating hole 15, a carbide, which is a conductive substance, is generated as a layer or a series of particles, and the carbide constitutes conductive layer 18. Furthermore, of the oxide which is a component of the material, a portion which has not reacted with carbon is sintered to be a sintered compact having a predetermined strength. The sintered compact serves as a frame portion in low-adhesive material 17, that is, base material 14. Therefore, according to the mold for molding a resin in the modification, base material 14 having a predetermined strength, communicating holes 15 having a uniform diameter and uniformly dispersed, and conductive layer 18 produced on the inner wall of communicating hole 15 are formed in the same process.

In the process of manufacturing low-adhesion material 17, the mixing ratio of oxide particles and carbon particles, the particle size of each material, the burning condition, and the like may be changed. Thereby, the average diameter of communicating hole 15 and resistivity, permeability, porosity, and compression strength of low-adhesion material 17 can be changed, and thus it becomes possible to manufacture low-adhesion material 17 having a different specification.

According to the mold for molding a resin in the modification, an effect similar to that obtained by mold for molding a resin using low-adhesion material 13 shown in FIG. 4 can be obtained. In addition, effects as will be described below can also be obtained.

Firstly, since the mold for molding a resin (upper mold 1 shown in FIGS. 2 and 3) itself generates heat, it becomes possible to increase the temperature of the mold for molding a resin to reach a predetermined temperature in a short period of time and with less energy. Therefore, energy used in the mold for molding a resin is reduced.

Secondly, an effect as will be described below can be obtained. After resin molding is performed numerous times, a component made of an organic substance adheres to each of mold surface 6 and the inner wall of communicating hole 15. Communicating hole 15 may clog due to the adhering matter. In this case, the adhering matter should be removed. According to the mold for molding a resin in the present embodiment, the adhering matter can be dissolved and removed by allowing the mold for molding a resin itself to generate heat until the temperature of mold surface 6 and the inner wall of communicating hole 15 reaches an evaporating temperature of the adhering matter. Therefore, clogging of communicating hole 15 can be prevented.

Further, in the mold for molding a resin in the modification, a protective film made of an inorganic material such as a glass-based material or a ceramics-based material, or an organic material such as a silicone-based resin or a fluorine-based resin may be formed as appropriate on the surface of low-adhesion material 17, that is, on mold surface 6, such that opening 16 of communicating hole 15 is not closed. The protective film not only has a function as an insulating film, but also has a function of protecting mold surface 6, a function of suppressing thermal conduction from low-adhesion material 17 to another member to enhance efficiency of heat effect, and a function of further improving releasability between the mold surface and the cured resin.

Although explanation has been given on the mold for molding a resin used when chip 8 mounted on substrate 7 is sealed with a resin in the second and the third embodiments, the mold for molding a resin of the present invention is not limited to the aforementioned mold for molding a resin, and may be the one used when a fluid resin injected into cavity 5 is cured to form a molded body as in transfer molding, injection molding, or other similar common techniques.

Further, although explanation has been given on transfer molding in the second and the third embodiments, resin molding performed using the mold for molding a resin of the present invention is not limited to transfer molding, and may be resin molding in which a fluid resin is injected into cavity 5, mold closing is performed, and then a cured resin is formed. For example, it is also possible to use the mold for molding a resin of the present invention in resin molding in which cavity 5 is filled with a fluid resin by potting, or resin molding in which a solid resin material supplied to cavity 5 is melted to fill cavity 5 with a fluid resin.

Furthermore, although entire mold surface 6 is made of a material with high releasability in the second and the third embodiments, the structure of the mold for molding a resin of the present invention is not limited to such a structure, and a portion of mold surface 6, for example only the top surface of cavity 5 (the upper surface in the drawing), may be made of a material with high releasability.

Further, although the low-adhesion material of the present invention is used for the mold surface of the mold for molding a resin, the application of the low-adhesion material is not limited to the one described above. The low-adhesion material may be used as a material for any part which requires a low adhesion property with respect to a fluid resin. Specifically, it is conceivable to use the low-adhesion material of the present invention for coating or other processing of a portion of such as a duct with which a fluid resin comes into contact.

Furthermore, it is conceivable that the low-adhesion material of the present invention is used in a portion which requires a low adhesion property with respect to an organic substance other than a fluid resin and a cured resin. For example, the low-adhesion material of the present invention can be used as a material having a function of preventing adhesion of a contaminant made of an organic substance. Specifically, it is conceivable that the low-adhesion material of the present invention is used as a material for a building material used for such as an outer wall of a building, a bathtub, sanitary chinaware, or other similar equipment. The low-adhesion material of the present invention may also be used as a material for coating the surface of a material used for these applications.

Although the present invention has been described and illustrated in detail, it is clearly understood that the same is by way of illustration and example only and is not to be taken by way of limitation, the spirit and scope of the present invention being limited only by the terms of the appended claims.

The invention claimed is:

1. A method of evaluating an adhesion property comprising the steps of:
    calculating a value of field strength of each of a plurality of oxides, where said value of field strength of each of said plurality of oxides is a value obtained by dividing a valence of a metal cation contained in one oxide of said plurality of oxides by a square of a sum of an ionic radius of said metal cation and an ionic radius of an anion contained in said one oxide;

measuring a value of adhesion strength between each of said plurality of oxides and an organic substance by experiment;

graphically representing a corresponding relationship between the value of field strength and the value of adhesion strength for each of said plurality of oxides;

determining a reference value for comparison of an adhesion property in said corresponding relationship;

calculating a value of field strength of another oxide, said value of field strength of another oxide being a value obtained by dividing said valence of said metal cation contained in said another oxide by a square of a sum of an ionic radius of said metal cation and an ionic radius of an anion contained in said another oxide; and evaluating an adhesion property of said another oxide by comparing said value of field strength of another oxide with said reference value for comparison.

* * * * *

UNITED STATES PATENT AND TRADEMARK OFFICE
CERTIFICATE OF CORRECTION

| | | |
|---|---|---|
| PATENT NO. | : 7,614,293 B2 | Page 1 of 1 |
| APPLICATION NO. | : 10/571683 | |
| DATED | : November 10, 2009 | |
| INVENTOR(S) | : Takaki Kuno et al. | |

It is certified that error appears in the above-identified patent and that said Letters Patent is hereby corrected as shown below:

Item (30), the Foreign Application Priority Data:

--March 26, 2004   (JP) ................. 2004-090894(P)-- should be shown.

Signed and Sealed this

Thirtieth Day of March, 2010

David J. Kappos
*Director of the United States Patent and Trademark Office*